United States Patent [19]
Dektar et al.

[11] Patent Number: 5,591,400
[45] Date of Patent: Jan. 7, 1997

[54] METHOD FOR PRODUCING AN IONIC SENSOR

[75] Inventors: John L. Dektar, Laguna Hills; Sanjay L. Patil, Irvine, both of Calif.

[73] Assignee: Minnesota Mining and Manufacturing Company, St. Paul, Minn.

[21] Appl. No.: 332,244

[22] Filed: Oct. 31, 1994

[51] Int. Cl.$^6$ .................................................. G01N 21/64
[52] U.S. Cl. ..................... 422/57; 422/82.08; 427/163.2
[58] Field of Search .............................. 422/82.05, 82.06, 422/82.07, 82.08, 55, 57; 436/172; 427/162, 163.2

[56] References Cited

U.S. PATENT DOCUMENTS

| | | | |
|---|---|---|---|
| 4,798,738 | 1/1989 | Yafuso et al. | 427/2 |
| 4,803,049 | 2/1989 | Hirschfeld et al. | 422/58 |
| 4,925,268 | 5/1990 | Iyer et al. | 350/96.29 |
| 4,978,503 | 12/1990 | Shanks et al. | 422/58 |
| 5,019,350 | 5/1991 | Rhum et al. | 422/82.07 |
| 5,028,395 | 7/1991 | Sebille et al. | 422/82.06 |
| 5,039,492 | 8/1991 | Saaski et al. | 422/82.09 |
| 5,081,041 | 1/1992 | Yafuso et al. | 436/68 |
| 5,093,266 | 3/1992 | Leader et al. | 436/68 |
| 5,098,659 | 3/1992 | Yim et al. | 422/82.07 |
| 5,114,676 | 5/1992 | Leiner et al. | 422/82.06 |
| 5,273,716 | 12/1993 | Northrup et al. | 422/82.07 |
| 5,319,975 | 6/1994 | Pederson et al. | 73/335.01 |

FOREIGN PATENT DOCUMENTS

| | | |
|---|---|---|
| 0263693 | 4/1988 | European Pat. Off. . |
| 0340018 | 11/1989 | European Pat. Off. . |
| 0568274A1 | 11/1993 | European Pat. Off. . |
| WO85/02679 | 12/1984 | WIPO . |

OTHER PUBLICATIONS

Munkholm, C. "Polymer Modification of Fiber Optic Chemical Sensors as a Method of Enhancing Fluorescence Signal for pH Measurement" Analytical Chemistry, vol. 58, pp. 1427–1430 (1986).

*Primary Examiner*—Jeffrey Snay
*Attorney, Agent, or Firm*—Gary L. Griswold; Walter N. Kirn; F. Andrew Ubel

[57] ABSTRACT

The present invention provides processes for the preparation of ionic sensors that include a matrix material, such as ion-permeable cellulose, having a sensing component included therein, such as a fluorescent dye, and an opaque overcoat material. For example, the present invention provides a method of making an ionic sensor comprising: contacting a water-swellable ion-permeable matrix material with an aqueous-based bath of a sensing component, or precursor thereof, under conditions effective to covalently attach the sensing component, or precursor thereof, to the water-swellable ion-permeable matrix material; wherein the aqueous-based bath comprises water and an organic solvent in an amount effective to solubilize the sensing component, or precursor thereof; contacting the water-swellable ion-permeable matrix material having covalently attached sensing component, or precursor thereof, with an aqueous solution having a pH of at least about 10 and an ionic strength of at least about that of a 5% aqueous sodium chloride solution to form a sensing element; and covering the sensing element with an opaque overcoat material. Also provided is a method of making a precursor to a preferred sensing component, i.e., acetoxypyrenetris(sulfonyl)chloride, which is made using a thionyl chloride method. If the sensing component is attached to the matrix material using amine groups, any unreacted amine groups can be capped by contacting them with a solution comprising an acetylating agent, an organic amine, and an ethereal solvent.

17 Claims, 1 Drawing Sheet of the sensing component and attachment of the sensing component to the matrix material. These processing steps are preferably used in the preparation of a sensor in which the overcoat is applied to a sensing element after the sensing component is attached to the matrix material. Preferred embodiments of the overall process require considerably less time than conventional processes, use and generate fewer toxic materials, produce sensors having more consistent pKa values, and produce sensors having more consistently high pKa values, preferably at least about 6.90 at 37° C.

METHOD FOR PRODUCING AN IONIC SENSOR

FIELD OF THE INVENTION

The invention relates to a system for sensing ionic species. More particularly, the invention relates to sensors, and methods for making sensors, useful in sensing ionic species in fluids, such as blood.

BACKGROUND OF THE INVENTION

In modern medical practice, an important indicator of a patient's condition is the concentrations of gases and ions dissolved in the blood. Traditionally, ionic and gaseous species were measured by removing a sample of blood and assaying it by electrochemical techniques. More recently, direct contact measurements made by sensors placed within the vascular system have been used. Such sensors can be electrochemical in nature or optically based, for example.

In one type of optical blood sensor a matrix material is treated with a sensing component suitable for providing a signal that varies as the concentration of the species of interest varies. Generally, this sensing component is covalently bonded to the matrix material, although this is not always a requirement. This matrix material and sensing component constitute a sensing element. In one such sensor, the sensing component is a fluorescent dye and the matrix material is a cellulose membrane sheet. A small disc is cut from the membrane sheet and is placed in a well of a sensor cassette, which itself is placed in proximity to an optical fiber. An opaque overcoat material can be physically placed over the exposed surface of the disc and secured to the cassette. This overcoat, which is physically separate from the disc, provides optical isolation for the dye in the sensing element. An alternative type of construction includes a disc of cellulose membrane with a fluorescent dye covalently bonded thereto and an overcoat material which is also covalently attached to the disc (see U.S. Pat. No. 5,081,041). In either type of construction, when the sensing component is excited by light imposed on the sensing component, it undergoes fluorescence, emitting a signal. This emission signal is transmitted by the optical fiber to a processor where it is analyzed to provide a determination of the concentration of the species of interest.

Known techniques for preparing such sensors have certain limitations. In some instances, the process requires an inconveniently long time for certain reactions to come to completion. In others, the process requires the use of reagents, or produces intermediates or byproducts, that are toxic. Furthermore, the consistency between sensors which are cut from different parts of the same membrane sheet has been inadequate to provide sensors at the lowest possible cost to the public. Also, certain of the known techniques do not provide adequate sensitivity to the finished device, as a result of low and variable dye concentrations and pKa values.

SUMMARY OF THE INVENTION

The present invention addresses the above-identified limitations in the art by providing an overall process for making a sensor that is easily scaled up for commercial production, uses fewer toxic reagents than were previously required, and provides more consistent results and good sensitivity as a result of generally higher and more uniform dye concentrations and pKa values. The overall process involves various improved processing steps related to the formation of the sensing component and attachment of the sensing component to the matrix material. These processing steps are preferably used in the preparation of a sensor in which the overcoat is applied to a sensing element after the sensing component is attached to the matrix material. Preferred embodiments of the overall process require considerably less time than conventional processes, use and generate fewer toxic materials, produce sensors having more consistent pKa values, and produce sensors having more consistently high pKa values, preferably at least about 6.90 at 37° C.

Specifically, the present invention provides a method of making an ionic sensor comprising: contacting a water-swellable ion-permeable matrix material with an aqueous-based bath of a sensing component, or precursor thereof, under conditions effective to covalently attach the sensing component, or precursor thereof, to the water-swellable ion-permeable matrix material; wherein the aqueous-based bath comprises water and an organic solvent in an amount effective to solubilize the sensing component, or precursor thereof; contacting the water-swellable ion-permeable matrix material having covalently attached sensing component, or precursor thereof, with an aqueous solution having a pH of at least about 10 and an ionic strength of at least about that of a 5% aqueous sodium chloride solution to form a sensing element; and covering the sensing element with an opaque overcoat material.

The present invention also provides a method of making an ionic sensor comprising: reacting acetoxypyrenetris(sulfonyl)chloride with an amine-modified polymeric ion-permeable matrix material to form bound acetoxypyrenesulfonamide; wherein the acetoxypyrenetris(sulfonyl)chloride is made by a method comprising converting hydroxypyrenetrisulfonate to acetoxypyrenetrisulfonate and reacting acetoxypyrenetrisulfonate with thionyl chloride and a catalytic amount of disubstituted formamide to form acetoxypyrenetris(sulfonyl)chloride; converting the bound acetoxypyrenesulfonamide to the hydroxy form, i.e., hydroxypyrenesulfonamide, to form a sensing element; and covering the sensing element with an opaque overcoat material.

The present invention further provides a method of making an ionic sensor comprising: applying to a surface of a first polymeric ion-permeable matrix material, a second polymeric ion-permeable matrix material having mixed therein an opaque agent; reacting both matrix materials with an epoxide having at least two epoxy groups per molecule to covalently bond the two matrix materials together and form pendant epoxy groups; reacting the epoxy groups with an organic amine having at least two amine groups per molecule to form pendant amine groups; reacting acetoxypyrenetris(sulfonyl)chloride with the pendant amine groups in an aqueous-based bath comprising water, an organic solvent in an amount effective to solubilize the acetoxypyrenetris(sulfonyl)chloride, and buffer salts, to form bound acetoxypyrenesulfonamide; wherein the acetoxypyrenetris(sulfonyl)chloride is made by a method comprising converting hydroxypyrenetrisulfonate to acetoxypyrenetrisulfonate and reacting acetoxypyrenetrisulfonate with thionyl chloride and a catalytic amount of a disubstituted formamide to form acetoxypyrenetris(sulfonyl)chloride; converting the bound acetoxypyrenesulfonamide to the bound hydroxy form; and capping any unreacted amine groups on the matrix material by contacting the unreacted amine groups with a solution comprising an acetylating agent, an organic amine, and an ethereal solvent.

In addition to these methods, the present invention provides an ionic sensor for sensing the concentration of an ionic species in a medium comprising: a sensing element comprising a polymeric ion-permeable matrix material and a sensing component attached to the polymeric ion-permeable matrix material through epoxide and amine linking groups; wherein the sensing component is present in an amount effective to provide a signal that varies as the concentration of the ionic species in the medium varies; and an opaque overcoat material covering the sensing element; wherein the opaque overcoat material is applied after the sensing component is attached to the matrix material.

DETAILED DESCRIPTION OF THE INVENTION

Figure 1:
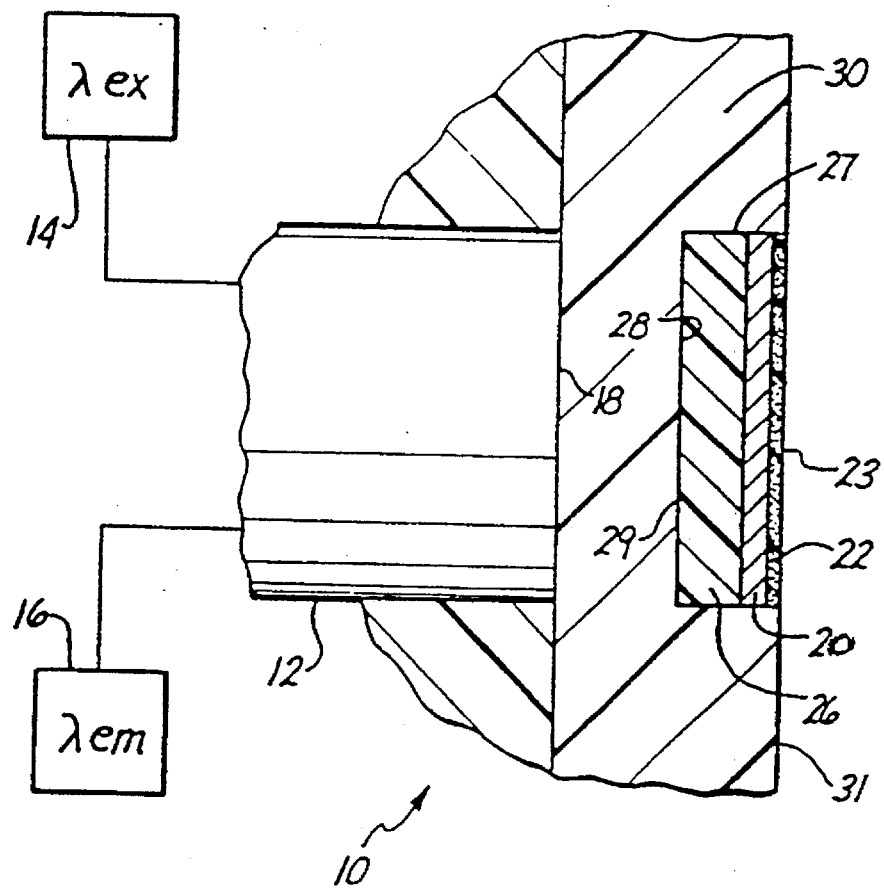
FIG. 1 is a schematic illustration of a sensor apparatus according to the present invention.

The present invention provides processes for the preparation of ionic sensors that include a matrix material, such as ion-permeable cellulose, having a sensing component included therein, such as a fluorescent dye, and an opaque overcoat material. The combination of matrix material and sensing component are referred to herein as the sensing element. The sensing element includes a sensing component in an amount effective to provide a signal, which varies in response to variations in the concentration of the ionic species of interest in the monitored medium. The opaque overcoat material can be, for example, a layer of ink, a black membrane, or a second matrix material, such as dextran, having an opaque agent, such as carbon black, included therein in an amount effective to render the second matrix material opaque. The opaque overcoat material can be physically separate from the sensing element, or it can be in direct contact with it as, for example, in the sensor disclosed in U.S. Pat. No. 5,081,041. The processes of the present invention can be used to prepare either type of sensor.

These processes provide sensors with highly reliable sensing signals that are highly responsive to changes in the concentration in the ionic species of interest in the medium being monitored. They have more uniform dye concentrations, more consistent pKa values, and more consistently high pKa values. Preferably, the sensors of the present invention have pKa values of at least about 6.90, and more preferably at least about 6.95, at a temperature of about 37° C.

The sensing elements of the present invention are useful in a method for sensing the concentration of an ionic species in a medium, preferably a fluid medium, and in particular blood. The medium to be monitored is first contacted with the sensing element and the sensing component in the sensing element emits a signal, which is dependent on the concentration of the ionic species of interest in the medium being monitored. This "emission" signal is analyzed using techniques which are known in the art, to determine the concentration of the ionic species of interest in the medium being monitored.

Sensing Component

Any suitable sensing component can be employed in the sensing elements of the present invention provided that the sensing component has no substantial detrimental effect on the function of the present system or on the medium being monitored. The sensing component is preferably an optical indicator, such as absorbance indicator or a fluorescence indicator. More preferably, the sensing component is a fluorescence indicator. The sensing component is particularly useful in sensing the concentration of hydrogen ions ($H^+$), hydroxyl ions ($OH^-$), and metal ions such as alkali and alkaline earth metal ions. In this embodiment, the pH of the medium is the most often determined. Suitable pH sensing components include many well known pH indicators and/or functionalized derivatives of such indicators. Among the useful pH sensing components are hydroxypyrenetrisulfonic acid and derivatives, e.g., salts, thereof, phenolphthalein, fluorescein, phenol red, cresol red, pararosaniline, magenta red, xylenol blue, bromocresol purple, bromphenol blue, bromothymol blue, metacresol purple, thymol blue, bromophenol blue, bromothymol blue, tetrabromophenol blue, bromchlorphenol blue, bromocresol green, chlorpheno red, o-cresolphthalein, thymolphthalein, metanil yellow diphenylamine, N,N-dimethylaniline, indigo blue, alizarin, alizarin yellow GG, alizarin yellow R, congo red, methyl red, methyl violet 6B, 2,5-dinitrophenol, and/or the various functionalized derivatives of the above species. Sensing components for other ionic species can be made from organic species which include fluorescein, diiodofluorescein, dichlorofluorescin, phenosafranin, rose bengal, eosin I bluish, eosin yellowish, magneson, tartrazine, eriochrome black T, coumarin, alizarin, and others. The preferred pH sensing component is hydroxypyrenetrisulfonic acid, derivatives of hydroxypyrenetrisulfonic acid, and mixtures thereof.

A particularly preferred sensing component, e.g., sensing dye, for use in making the sensor element is hydroxypyrenetrisulfonic acid, which when bound to the matrix material is in the form of a sulfonamide. Conventionally, this dye is made by preparing the acylated form of hydroxypyrenetrisulfonate (HPTS), which is a solid, and reacting this with solid $PCl_5$ by grinding the two together. The resultant product is acetoxypyrenetris(sulfonyl)chloride (APTSC), which is then attached to the matrix material and then converted to the hydroxy form. APTSC prepared by this method typically includes impurities that are difficult to remove. These impurities cause sensing elements to have low and variable pKa values. It has been discovered that APTSC can be made by a more convenient reaction procedure that provides a purer product and is more conducive to large scale production. This method involves converting HPTS to acetoxypyrenetrisulfonate (APTS) and then converting this to APTSC using thionyl chloride and a disubstituted formamide. The thionyl chloride is used in a large stoichiometric excess relative to the APTS. The disubstituted formamide is used in a catalytic amount, preferably in an amount of about 1:100 to 1:1000 (parts disubstituted formamide to parts of APTS). The disubstituted formamide can be substituted with any alkyl or aryl groups that do not interfere with the conversion of APTS to APTSC. It is preferably substituted with ($C_1$–$C_8$)alkyl groups, ($C_5$–$C_{10}$)aryl groups (including alkyl-substituted aryl groups), or combinations thereof. Suitable examples include, dimethyl formamide, dibenzyl formamide, benzyl methyl formamide, phenyl methyl formamide, and the like. A particularly preferred disubstituted formamide is dimethyl formamide.

Specifically, this method includes the steps of: preparing a warm solution (i.e., about 20°–70° C., preferably about 40°–50° C.) of a large excess (preferably a 10–50 fold excess) of acetic anhydride relative to the HPTS in dimethyl formamide as the solvent; adding HPTS and sodium acetate (preferably in an amount of between a stoichiometric amount and a 3-fold excess relative to the amount of HPTS) to the solution and allowing a reaction to take place;

stripping off the solvent to recover acetoxypyrenetrisulfonate (APTS); and refluxing the APTS with thionyl chloride and a catalytic amount of disubstituted formamide under a dry, oxygen-free (preferably, inert) atmosphere thereby forming acetoxypyrenetris(sulfonyl)chloride. Preferably, the method also includes the steps of recovering the acetoxypyrenetris(sulfonyl)chloride by washing the product in an organic solvent and then stripping off the organic solvent. This method of chlorinating APTS via a thionyl chloride reaction has several advantages over known methods of synthesizing APTSC, including easier scale-up for commercial applications, easier removal of reaction byproducts (which are generally either insoluble or volatile) from the desired product, and the avoidance of unwanted side reactions between the chlorinating agent and the matrix material of the sensing element. This purer product of APTSC results in a sensing element having more consistent and higher pKa values.

The amount of sensing component employed in the sensing element should be sufficient to provide an ionic species concentration-dependent signal which is of sufficient intensity to be transmitted and analyzed in determining the concentration of the ionic species of interest in the medium being monitored. The specific amount of sensing component employed varies depending, for example, on the specific sensing component being employed, the ionic species being sensed, the medium being monitored, and the other components of the sensor system being employed.

Matrix Material

The matrix material in the sensing element, i.e., the first matrix material, as well as the matrix material in the overcoat (if such a construction is used), i.e., the second matrix material, are permeable to the ionic species of interest, and are preferably substantially insoluble in the medium to be monitored. That is, the first and second matrix materials should be structured so that the ionic species of interest can physically permeate such matrix materials. Any suitable first and second matrix materials can be employed provided that such matrix materials have no substantial detrimental effect on the functioning of the system or on the medium being monitored. Preferred ion-permeable matrix materials are water-swellable, as is cellulose.

Each of the first and second matrix materials is preferably a polymeric material. The matrix materials can be in the form of a membrane, particles, fibers, etc. Macromolecular hydrophilic polymers that are substantially insoluble in the medium to be monitored and permeable to the ionic species of interest are particularly useful as first and/or second matrix materials in systems used to monitor aqueous media. Such polymers include, for example, ion permeable cellulosic materials, high molecular weight or crosslinked polyvinyl alcohol (PVA), dextran, crosslinked dextran, polyurethanes, quaternized polystyrenes, sulfonated polystyrenes, polyacrylamides, polyhydroxyalkyl acrylates, polyvinyl pyrrolidones, hydrophilic polyamides, polyesters and mixtures thereof. Preferably, the second matrix material is crosslinked (if it is used). More preferably, both the first and second matrix materials are crosslinked. In a particularly useful embodiment, the first matrix material is cellulosic, especially ion permeable crosslinked cellulose. With a cellulosic first matrix material, the second matrix material (if it is used) is preferably derived from dextran, and is more preferably crosslinked dextran. Each of the first and second matrix materials, in particular the second matrix material, can be derived from one or more water soluble materials.

The matrix material polymers can be anionic or cationic in character, as desired, and can be made so using conventional and well known techniques. For example, such polymers, or functionalized derivatives thereof, can be reacted with an acidic component, such as an organic sulfonic acid, a carboxylic acid, and the like to form anionic polymers; or can be reacted with a basic component, such as an organic amine and the like, to form cationic polymers.

The amount of first matrix material used can vary depending, for example, on the specific first matrix material and sensing component being employed. Such first matrix material is preferably present in an amount effective to act as a carrier for the sensing component and/or as a filler to provide additional volume. Since the first matrix material is permeable to the ionic species of interest, this first matrix material facilitates interaction between this ionic species and the sensing component which results in the ionic species concentration variable signal, described herein. The sensing component is preferably substantially uniformly distributed in the first matrix material. The amount of second matrix material used may vary depending, for example, on the specific second matrix material and opaque agent being employed. Such second matrix material preferably acts as a carrier or binder to provide additional volume.

Sensing Element

The sensing component can be bonded, physically or chemically, to the first matrix material to form the sensing element. Alternatively, the sensing element can include a physical mixture containing the sensing component and first matrix material. The sensing component is preferably chemically bonded, more preferably covalently bonded, to the first matrix material. Chemical bonding of the sensing component to the first matrix material can be accomplished either by direct coupling of the sensing component to reactive sites on the first matrix material, as for instance, the hydroxyl groups on either cellulose or PVA, or through indirect coupling utilizing a substituent group, e.g., epoxy linkages, amine linkages, or both, which is coupled or chemically bound to the first matrix material.

Preferably, the first matrix material has hydroxyl (—OH) groups or carboxyl (—COOH) groups, and more preferably hydroxyl groups. In modifying the matrix material for coupling with the sensing component, these —OH functional groups are preferably reacted with an epoxide, i.e., a compound with two or more epoxy groups per molecule, to form an epoxy-modified matrix material. This causes crosslinking of the cellulose and provides pendant epoxy functional groups. Preferably, the epoxide is a diepoxide. An organic amine, i.e., an organic compound with two or more amino groups per molecule, is then reacted with the epoxy-modified matrix material. Preferably, the organic amine is a diamine. The sensing component is then combined with this amine-modified matrix material. In this way, the sensing component is attached to the matrix material through epoxide and amine linking groups.

The sensing component is preferably attached to the first matrix material before an overcoat material is applied. Preferably, a complete sensing element is produced before the overcoat material is applied. Alternatively, however, the sensing component can be attached to the first matrix material after the overcoat is applied, as is disclosed in U.S. Pat. No. 5,081,041, the description of which is incorporated herein by reference. Briefly, this involves applying to a surface of a first matrix material, e.g., cellulose, a second matrix material, e.g., dextran, having an opaque agent, e.g., carbon black, mixed therein. These two matrix materials are then crosslinked, and thereby covalently bonded together, with an epoxide, which also results in the formation of pendant epoxy groups. These pendant epoxy groups are then reacted with an organic amine to form pendant amine groups. The desired sensing component, or precursor thereof, is then attached to the combined matrix materials through the amine groups.

In a preferred embodiment of the present invention, a polymeric matrix material containing hydroxyl groups, preferably ion permeable cellulose, is combined with an epoxide under conditions that cause crosslinking of the cellulose and formation of pendant epoxy groups. Preferably, the conditions are such that they minimize the amount of crosslinking of the cellulose and maximize the formation of pendant epoxy groups. The resultant epoxy-modified cellulose is then combined with an organic amine under conditions that cause formation of pendant amine groups. Preferably, the conditions are such that they minimize the further crosslinking of the cellulose and maximize the formation of pendant amine groups. The pendant amine groups are then available for reaction with the sensing component or sensing component precursor to join the sensing component to the cellulose.

The epoxide can be any epoxide having at least two epoxy groups per molecule that performs the desired function. Suitable examples include ethylene glycol diglycidyl ether, butanediol diglycidyl ether, polyethylene glycol diglycidyl ether, epoxy resins having at least two epoxy groups per molecule, and the like. The organic amine can be any aryl or alkyl amine having at least two amine groups per molecule that performs the desired function. Suitable examples include, hexane diamine, 1,8-diamino-3,6-dioxaoctane, and JEFFAMINE polyether diamine (available from Texaco, Inc., Houston, Tex.), for example. Preferably, the organic amine is a diamine, and more preferably a $(C_2-C_{20})$alkyl diamine or a $(C_6-C_{10})$aryl diamine.

The reaction with the epoxide is typically carried out in the presence of a basic material, such as sodium hydroxide, to promote the reaction between the —OH functionality and the epoxide. It can also be carried out in the presence of a permeability agent that acts to maintain the first matrix material sufficiently porous so the resultant sensing element is permeable to the ionic species of interest. The permeability agent is preferably chosen such that it has no substantial detrimental effect on the method of making the sensing element. One particularly useful permeability agent is dimethyl sulfoxide (DMSO).

Preferred reaction conditions that promote a small amount of crosslinking of the first matrix material and the formation of a high concentration of pendant epoxy groups include a large excess of epoxide to cellulose, a short reaction time (preferably less than about 12 hours, more preferably less than about 30 minutes, and most preferably about 2–4 minutes), and a low temperature (preferably about 10°–50° C.). Preferred reaction conditions that promote a small amount of crosslinking of the first matrix material and the formation of high concentration of pendant amine groups include a large excess of amine, a short reaction time (e.g., less than about 12 hours, more preferably less than about 30 minutes, and most preferably about 2–4 minutes), and a low temperature (preferably about 10°–60° C.).

The first matrix material, preferably modified with amine groups, is contacted with a sensing component or a sensing component precursor at conditions effective to form a sensing element including the sensing component in an amount effective to provide a signal which varies as the concentration of the ionic species in the medium varies. The contacting step can be repeated one or more times to provide the desired amount of sensing component in the matrix material. Although the sensing component can be physically combined or mixed with the first matrix material, it is preferably chemically bonded, more preferably covalently bonded, to the first matrix material. As stated above, this occurs preferably before the overcoat, e.g., second matrix material having an opaque agent therein, is applied to or over the sensing element.

Attaching the sensing component to the first matrix material is carried out by dissolving the sensing component in a solvent and soaking the matrix material in this solution for a time effective to provide the desired sensing intensity. Conventionally, for the preferred hydroxypyrenetrisulfonic acid dye, dimethyl formamide (DMF) was used as the solvent; however, this caused the preferred cellulose matrix material to shrink as a result of the pores collapsing, and an inconsistent and nonuniform concentration of sensing dye attached to the cellulose. It has been discovered that this can be avoided for cellulose and other water-swellable matrix materials by using an aqueous-based bath. Preferably, the solvent for the bath is a mixture of water and an organic solvent or surfactant, preferably an organic solvent, that can disperse or solubilize the sensing component or precursor thereof (preferably the precursor APTSC) and form a homogeneous solution or dispersion with water. The organic solvent is one that does not react with the sensing component or precursor thereof, but solubilizes or disperses it. Examples of suitable organic solvents for solutilizing APTSC include acetone or acetonitrile. A particularly preferred organic solvent is acetone. The organic solvent or surfactant are used in relative amounts such that the sensing component is solubilized and the matrix material does not dry out and shrink as a result of pores collapsing. More preferably, the organic solvent and water are used in amounts of about 0.4:1 to 2.4:1 (parts organic solvent to parts water).

Most preferably, the aqueous-based bath (e.g., dye bath) includes suitable solvents, the sensing component or precursor of choice, preferably APTSC, and buffer salts effective to maintain the appropriate pH of the solution so the matrix material, preferably cellulose, remains expanded. Preferably, the buffer salts are those water soluble inorganic salts that are effective buffers in a pH range of 8–11. Examples of suitable buffer salts are sodium carbonate, sodium bicarbonate, sodium monobasic phosphate, sodium dibasic phosphate, sodium borate, and the like, which can be used in various combinations. It should be understood that the sodium ions of these salts can be replaced by other salt forming ions for other suitable buffer salts. Preferred buffer salts are sodium carbonate and sodium bicarbonate. The buffer salts can be used in a wide variety of amounts, depending on the concentration of the sensing component or precursor in the bath, the desired pH of the solution (for the amine to react with the APTSC, the pH should be greater than 7), the desired reaction time, etc. These amounts and appropriate pH can be readily determined by one of skill in the art.

Preferably, the matrix material is contacted with the sensing component bath for a time effective to cause the sensing component to become bound thereto. Prior to allowing the sensing component bath to contact the matrix material it can be aged to reduce the number of reactive sites. For example, APTSC is aged for a period of time in a buffered acetone/water solution to hydrolyze a portion of the reactive sites, preferably for a period of time effective to form one reactive site per molecule. Thus, once the APTSC is combined with amine-modified cellulose, for example, it can form one, two, or three sulfonamide linkages per molecule, depending on whether it is aged or not and depending on the length of time it is aged. Preferably, the APTSC is aged a sufficient amount of time that only one sulfonamide linkage is formed per molecule upon binding to the matrix material.

Typically, the resultant sensing element has covalently bound molecules of the sensing component or a precursor thereof (e.g., APTSC bound through sulfonamide linkage(s) referred to herein as acetoxypyrenesulfonamide). It can also have unreacted amine groups, which can detrimentally effect the pKa of the sensing element. These amine groups can be capped, i.e., convened to noninterfering groups, by a variety of methods. Conventionally, the unreacted amine groups were capped using a two step process. First, acetic anhydride was used to form amide groups. Second, methane sulfonyl chloride was used in the presence of pyridine to form sulfonated amine groups.

It has been discovered that the use of methane sulfonyl chloride step can be eliminated, the acetylation step shortened considerably, and the amount of acetic anhydride lessened by using a solution containing an organic amine along with an acetylating agent in an organic solvent, preferably an ethereal solvent such as tetrahydrofuran, diethyl ether, or diglyme. This new and preferred acetylating process is typically carried out at room temperature (20°–25° C.) and occurs rather quickly (typically in less than about 5 minutes). It is faster, uses fewer reagents, and generates less hazardous waste than conventional processes used for fabricating fluorescent pH sensors, for example. It also provides a significant increase, e.g., about 0.04 units, in the pKa of the sensing element.

The acetylating agent is preferably acetic anhydride, although it can be other compounds capable of acetylating amine groups, such as acetyl chloride and acetate esters of N-hydroxy succinimide. The organic amine is a one that is capable of neutralizing the acid formed during the course of the reaction and is incapable of reacting with the acetylating agent. Preferably, the organic amine is a tertiary amine, such as triethylamine, pyridine, and substituted pyridines such as 4-dimethylaminopyridine, 4-pyrrolodinopyridine, cyclohexylaminopyridine, and the like. More preferably, the tertiary amine is triethylamine. Preferably, the organic amine is used in an amount of about two moles per mole acetylating agent.

Optionally, the solution can include a catalyst that is capable of enhancing the reaction rate of the acetylation. Preferably, the catalyst is a substituted pyridine. Suitable examples of such catalysts are 4-dimethylaminopyridine, 4-pyrrolodinopyridine, cyclohexylaminopyridine, and the like. More preferably, the catalyst is 4-dimethylaminopyridine. The catalyst is preferably used in an amount of about 0.1–100 mole-%, and more preferably about 0.1–2 mole-%, based on the amount of organic amine used.

It is believed that the sensing element can also have ionically bound sensing component, or precursor thereof, that can detrimentally effect the pKa of the sensing element by giving unstable and false high pKa values. It has been discovered that the ionically bound material can be removed using an aqueous solution having a pH of at least about 10 and a high ionic strength (i.e, at least about that of a 5% aqueous sodium chloride solution) thereby forming more consistent results, particularly with respect to the pKa of the sensing element. Preferably, the solution contains a base, such as sodium hydroxide or sodium carbonate, and an inorganic salt that provides the desired ionic strength. Examples of suitable inorganic salts include sodium chloride, sodium acetate, and sodium sulfate. These bases and salts can be used in various combinations. A particularly preferred embodiment includes sodium carbonate for a basic pH and sodium chloride for a high ionic strength. This step can be carried out before or after the unreacted amine groups are capped, or both if desired. Preferably, the reaction is carried out at a temperature and for a time effective to remove the ionically bound sensing component molecules. Typically, the effective temperature is about 20°–90° C., and preferably about 65°–75° C.

Ideally, this reaction step also converts the bound APTSC, which is in the form of a acetoxypyrenesulfonamide, to the preferred hydroxypyrenesulfonamide dye, which was conventionally done using a 2.5 wt-% aqueous sodium carbonate solution. Thus, the reaction is more preferably carried out at a temperature and for a time effective to remove the ionically bound sensing component molecules and convert the sensing component precursor to the sensing component. It should be understood that if there is no contamination from ionically bound sensing component, or precursor thereof, an aqueous sodium carbonate solution can be used without the sodium chloride to effect this conversion.

Overcoat

Any opaque overcoat material can be used provided that such overcoat functions to provide the desired degree of opacity for effective optical isolation of the sensing component, and have no substantial detrimental effect on the functioning of the present system or on the medium being monitored. It can be applied before, as described in U.S. Pat. No. 5,081,041, or after the sensing component is attached to the first matrix material. It can be directly attached to the sensing element or it can be separate from the sensing element. In preferred embodiments, it is applied after the sensing component is attached to the first matrix material.

The overcoat can be a matrix material as described above containing an opaque agent such as carbon black, or carbon-based opaque agents, ferric oxide, metallic phthalocyanines, and the like. Such opaque agents are preferably substantially uniformly dispersed in the second material in an amount effective to provide the desired degree of opacity to provide the desired optical isolation. A particularly useful opaque agent is carbon black. The overcoat can also be an ink coating on the sensing element applied using a variety of techniques, such as an ink-jet technique or an ink-screening technique. The overcoat can also be a black membrane stapled or heat-staked to the casette holding the sensing element. For example, it can be a black DURAPORE membrane (available from Millipore as a white membrane which is then treated with black ink) and heat sealed to the cassette.

Sensors

In a useful embodiment, where the pH of blood is being monitored using a hydroxypyrene trisulfonic acid sensing component, crosslinked cellulose is employed as the first matrix material, crosslinked dextran is employed as the second matrix material and carbon black as the opaque agent, the relative volume or thickness of the first material or first layer to the second material or second layer, respectively, is preferably in the range of about 1 to 0.01 to about 1 to 0.5. This type of sensor, in which the cellulose and dextran are covalently bonded together, is disclosed in U.S. Pat. No. 5,081,041, which is incorporated herein by reference.

FIG. 1 shows another embodiment of a pH sensor 10 of the invention, in which the overcoat is applied after the sensing element is formed, i.e., after the sensing component is attached to the matrix material. An optical fiber 12 is connected to a light transmitting apparatus 14. The light transmitting apparatus 14 generates the excitation light. The optical fiber 12 is also connected to a light receiving apparatus 16. The light receiving apparatus 16 receives and analyzes the emission light from the fluorescence sensing component.

The optical surface 18 of the fiber 12 is spaced apart from the sensing element, shown generally at 20. Sensing element 20, which is produced as described in the example herein, is covered by an opaque overcoat 22. A transparent polyurethane-based adhesive layer 26 bonds sensing element 20 to well 28. The thickness ratio of opaque overcoat 22 to sensing element 20 to adhesive layer 26 is about 1 to about 5 to about 100. Sensing element 20 is located in well 28 of cassette 30 as shown in FIG. 1. Well 28 is open at one end, includes a right circular cylindrical side wall 27 and a circular bottom wall 29. Well 28 has a diameter of 0.15 inches and a depth of 0.010±0.0005 inches. The top surface 23 of opaque overcoat 22 is substantially flush with the inner surface 31 of cassette 30. Cassette 30 is made of transparent polycarbonate. The sterility of the fluid flow path through cassette 30 is not disturbed by the presence of sensing element 20 in well 28.

In use, the fluid medium of which the pH is to be monitored, e.g., blood, is allowed to come into contact with sensing element 20 by flowing this medium in cassette 30 back and forth across sensing element 20 overcoated by opaque overcoat 22. Excitation light of an appropriate wave length from the light transmitting apparatus 14 is fed to the optical fiber 12, which transmits it toward sensing element 20. This excitation light interacts with the sensing component in the sensing element 20 to fluoresce and emit a signal which is dependent on the pH of the medium being monitored. The emission light from the fluorescence is transmitted by optical fiber 12 to light receiving apparatus 16 where it is processed and analyzed to determine the pH of the medium being monitored.

Objects and advantages of this invention are further illustrated by the following examples. The particular materials and amounts thereof recited in these examples as well as other conditions and details, should not be construed to unduly limit this invention. All materials are commercially available except where stated or otherwise made apparent.

EXAMPLE 1

Method of Preparing Sensor Dye

Preparation of Acetoxypyrenetrisulfate

The following reaction was performed in order to transform hydroxypyrenetrisulfonate (HPTS) to acetoxypyrenetrisulfonate (APTS). Acetic anhydride (125 ml) and dimethyl formamide (DMF, 1000 ml) were mixed in a flask. The mixture was heated to 45°±5° C. with continuous stirring. HPTS (25 g, commercially available from Eastman Fine Chemicals, Rochester, N.Y., product number 119 1774, as 8-hydroxy-1,3,6-trisulfonic acid trisodium salt) and sodium acetate (3.75 g) were added to the solution. The mixture was allowed to react while being maintained at 45° C. for about 90 minutes. The stirring bar was then removed, and the solvents were stripped off by treatment with a model RE121 rotoevaporator used with a Model 461 water bath (both commercially available from Büchi Co. of Switzerland). The rotoevaporator was set to 80° C. and the process of stripping the solvents required about 1.5 hours. The remaining material was vacuum oven dried in a NAPCO model 5831 vacuum oven (commercially available from Precision Scientific of Chicago, Ill.) set to full vacuum and to 60° C. for 30 minutes. The resultant product, APTS, was washed by adding 250 ml of methanol to the flask and stirring for 15 minutes. The product was then separated from the supernatant by vacuum filtration through a #5 filter (commercially available from Whatman of Maidstone, England). The product was vacuum oven dried on the filter in the vacuum oven described above, set to full vacuum and to 60° C. for 30 minutes.

Preparation of Acetoxypyrenetris(sulfonyl)chloride

The APTS was then converted to acetoxypyrenetris(sulfonyl)chloride (APTSC) as follows. The APTS from Example 1 was placed in a flask and 150 ml of thionyl chloride (commercially available from Aldrich Chemical Company of Milwaukee, Wis.) was added. Two drops of DMF (commercially available from Spectrum of Gardena, Calif.) was then added to the flask. A magnetic stirring bar was added and the mixture was heated with continuous stirring on a heat/stir plate. In this reaction system, a flask on a heat/stir plate was connected to a condenser via a gas inlet adapter having a gas inlet port. The gas inlet port was connected to a source of dry nitrogen via a tube. The condenser was connected to an inlet adapter, which was connected to a filter flask via a tube. The filter flask served as a dry trap and had a side port, which was connected by a tube to a flask. The flask was intended to be a wet trap. There was also a sparger tube extending below the level of a charge of water within the flask. A flow of nitrogen was initiated, regulated to about 1–2 psi (7–14 kPa), sufficient to generate a stream of bubbles within the liquid in the wet trap. The reaction flask was heated on the heat/stir plate to about 60° C.±5°, sufficient to reflux the solution in the condenser, providing a slow stream of solvent back to the reaction flask. This reflux was continued for 45 minutes.

The resultant APTSC was then removed from the solvent as follows. The rotoevaporator of Example 1 and a solvent receiver flask were carefully washed with isopropyl alcohol to remove all traces of water. The reaction flask described above was then mounted on the rotoevaporator and secured with a clamp. A teflon chambered vacuum pump was then connected to the rotoevaporator by way of a dry ice/isopropyl alcohol cooled trap. This trap was necessary to avoid excess thionyl chloride being drawn through the vacuum pump. A dry ice/isopropyl alcohol mixture was then placed in the rotoevaporator's trap, and the reaction flask rotoevaporated to dryness. The teflon vacuum pump was then connected directly to the flask for an additional 45 minutes. The reaction flask containing the APTSC was removed from the rotoevaporator, and the solvent in the solvent receiver was carefully neutralized and disposed of, taking regard for the residual thionyl chloride.

The APTSC was purified as follows: toluene (1000 ml) was warmed on a heat/stir plate to 80° C.±5°, stirring moderately. Half (500 ml) of the heated toluene was added to the flask containing the dried APTSC and the flask stirred and shaken well. The remainder of the toluene was then added to the flask, and the solution heated to boiling. The solution was then gravity filtered through a folded #5 whatman filter in a glass funnel. The filtrate was retained, and the cake discarded. The filtrate was then rotoevaporated to dryness. Room temperature (20°–25° C.) toluene (150 ml) was then added to the container bearing the dried product, and the material was scraped from the sides of the container and the solution mixed well. This liquid was again vacuum filtered through a whatman #5 filter, and the precipitate collected. The final purified APTSC was dried in the vacuum oven at 60° C. for 30 minutes.

EXAMPLE 2

Preparation of Sensing Element

Eight 22 cm×22 cm sheets of regenerated cellulose membrane (commercially available as CUPROPHAN from Membrana, a business of Enka AG of Ohderstrabe, Germany) were soaked in water and stretched over a glass plate. The excess water was removed by pipette. A plastic frame was clamped on the sheet-covered glass plate. A solution was prepared by mixing 40 g of 95% butanediol diglycidyl ether (commercially available from Aldrich), 240 g of a 50:50 w/w (weight/weight) mixture of dimethylsulfoxide (commercially available from Spectrum), deionized water, and 120 g of 0.75M sodium hydroxide solution. Fifty grams of this solution were poured onto each membrane, and the solution was allowed to react for 20 minutes. The membranes were then rinsed off with water, removed from the glass plates, and allowed to soak in a solution of 120 ml of 70% hexane diamine (commercially available from Eastman Fine Chemicals) mixed with 2 liters of deionized water, for 15 minutes. The membranes were then removed from this bath and washed with 1000 ml of deionized water three times.

A dye solution was prepared by dissolving 160 mg of acetoxypyrenetris(sulfonyl)chloride prepared according to conventional synthetic pathways via $PCl_5$ in 280 ml of acetone. To this was added 140 ml of a mixture made from 150 ml of 10 mM sodium carbonate and 50 ml of 10 mM sodium bicarbonate. This dye solution was then aged for 12 minutes. The treated membranes were allowed to react with this solution for various amounts of time depending on the intensity of fluorescence wanted from the finished membrane. The membranes were then removed from the dye solution, and placed in a bath of 2.5% w/w sodium carbonate and 10% w/w sodium chloride in water, which was held at 70° C. for 20 minutes. The membranes were then removed from the bath, rinsed with deionized water, blotted, and then soaked in a solution of 20% v/v (volume/volume) glycerol in 2.5% w/w sodium carbonate aqueous solution for 15 minutes. The membranes were then allowed to react for 5 minutes with a solution of 120 ml acetic anhydride, 75 ml of triethylamine, 1.5 g of 4-dimethylaminopyridine, and 480 ml of tetrahydrofuran. The membranes were then removed and soaked in a bath made from 800 ml of 2.5% w/w sodium carbonate and 10% w/w sodium chloride in water, which was held at 70° C., for 30 minutes. The membranes were then rinsed in deionized water and soaked in a solution of 20% v/v glycerol in water and dried.

EXAMPLE 3

Preparation and Evaluation of Sensor Cassette

Small round disks suitable to serve as sensor elements were punched out of the sensing membrane prepared as described in Example 2, and each was adhered to the end of an optical fiber with a urethane adhesive (commercially available as FLEXOBOND 431 from Bacon Co. of Irvine, Calif.). Each of the optical fibers was used to fabricate a sensor cassette of the type commercially available as Model 6701 from CDI/3M Health Care, of Tustin, Calif. Information on such cassettes is contained in U.S. Pat. Nos. 4,640,820; 4,786,474; 5,104,623; and 5,289,255. The sensor cassettes were then used with a model 5400 ex vivo blood gas analyzer (commercially available from CDI/3M Health Care) to measure the pH of known carbonate buffer solutions held at 37° C. Information on such analyzers, which include means to irradiate the sensor element with short wave radiation, means to measure the fluorescent response of the sensor element after irradiation by the irradiation means, and means to calculate a pH value in the liquid from the fluorescent response of the sensor, is contained in U.S. Pat. Nos. 4,557,900 and Re 31,879.

These measurements indicated that the $pK_a$ of the sensor disks was 6.91±0.02 at about 37° C. The intensity of the signal was found to be uniform to within 10% among sensors made from different membranes, and made from different locations on the same membrane after 24 samples were tested. These results were consistently better than stock Model 6701 sensor cassettes used as controls.

The sensor cassettes were subjected to a step change in pH by rapidly changing from one buffer solution to another while the time to reach a new equilibrium reading on the analyzer was noted. Among 24 samples tested, the time to reach substantially complete equilibration at the new reading level was approximately 60 seconds, a result which is acceptable for the application of practical blood gas sensing.

EXAMPLE 4

Preparation of Sensing Element

Sheets (22 cm×22 cm) of regenerated cellulose membrane, (commercially available as CUPROPHAN from Enka AK) were washed three times in at least 2000 ml of deionized water and stretched over a glass plate. The excess water was removed by pipette. A solution of 350 ml of dimethylsulfoxide (DMSO, commercially available from Spectrum) in deionized water was cooled to 20° C.±1°. This DMSO/water solution (640 ml) was then mixed into 100 g of 95% butanediol diglycidyl ether (commercially available from Aldrich), with stirring. A sodium hydroxide solution (16 g of 50% sodium hydroxide in 844 ml of deionized water) was then added to this mixture with stirring, and a timer started for 3 minutes of aging. The cellulose membranes were then submerged in the aged solution and left to react for 20 minutes to crosslink the membranes. After the described period, the reaction was halted by two washes of 2000 ml of deionized water.

A solution was prepared from 96 g of 70% hexane diamine (commercially available from Eastman Fine Chemicals) mixed with 1600 ml of deionized water. This solution was aged under stirring conditions for five minutes. During the aging, the pH of this solution was adjusted to 12±0.01 by adding 6N HCl solution dropwise as required. After the aging, the washed cellulose sheets were then allowed to soak in the solution for 20 minutes. After the described period, the reaction was halted by rinsing in 2000 ml of deionized water. The sheets were then rinsed two more times in 2000 ml of deionized water, and left to soak for 30 minutes in the final rinse.

A dye solution was prepared by dissolving 480 mg of acetoxypyrenetris(sulfonyl)chloride prepared according to Example 1 in 1070 ml of acetone. The membranes of Example 4 were cut into disks and tested according to the method of Example 3, except that 12 sensors where made from each of 9 different sheets. The $pK_a$ of these sensors was found to be 6.99±0.02 at about 37° C.

The sensor cassettes were subjected to a step change in pH by rapidly changing from one buffer solution to another, while the time to reach a new equilibrium reading on the analyzer was noted. Among 24 samples tested, the time to reach substantially complete equilibration at the new reading level was approximately 50 seconds, a result which is acceptable for the application of practical blood gas sensing.

While this invention has been described in connection with specific embodiments, it should be understood that it is capable of further modification. The claims herein are intended to cover those variations which one skilled in the art would recognize as the chemical equivalent of what has been described herein. Thus, various modifications to the principles described herein may be made by one skilled in the art without departing from the true scope and spirit of the invention which is indicated by the following claims.

What is claimed is:

1. A method of making an ionic sensor comprising:
   (a) contacting a water-swellable ion-permeable matrix material with an aqueous-based bath of a sensing component, or precursor thereof, under conditions effective to covalently attach the sensing component, or precursor thereof, to the water-swellable ion-permeable matrix material; wherein the aqueous-based bath comprises water and an organic solvent in an amount effective to solubilize the sensing component, or precursor thereof;
   (b) contacting the water-swellable ion-permeable matrix material having covalently attached sensing component, or precursor thereof, with an aqueous solution having a pH of at least about 10 and an ionic strength of at least about that of a 5% aqueous sodium chloride solution to form a sensing element; and
   (c) coveting the sensing element with an opaque overcoat material.

2. The method of claim 1 wherein the aqueous solution used in step (b) comprises:
   (a) a base selected from the group consisting of sodium carbonate, sodium hydroxide, and mixtures thereof; and
   (b) a salt selected from the group consisting of sodium chloride, sodium acetate, sodium sulfate, and mixtures thereof.

3. The method of claim 1 wherein the sensing component precursor is acetoxypyrenetris(sulfonyl)chloride, which is made by a method comprising:
   (a) converting hydroxypyrenetrisulfonate to acetoxypyrenetrisulfonate; and
   (b) reacting acetoxypyrenetrisulfonate with thionyl chloride and a catalytic amount of disubstituted formamide to form acetoxypyrenetris(sulfonyl)chloride.

4. The method of claim 1 wherein the aqueous-based bath is buffered.

5. The method of claim 4 wherein the aqueous-based bath is buffered with a salt selected from the group consisting of sodium carbonate, sodium bicarbonate, sodium monobasic phosphate, sodium dibasic phosphate, sodium borate, and mixtures thereof.

6. The method of claim 1, prior to the step of covalently attaching the sensing component, or precursor thereof, to the matrix, further including:
   (a) reacting the water-swellable ion-permeable matrix material with an epoxide having at least two epoxy groups per molecule to form an epoxy-modified matrix material; and
   (b) reacting the epoxy-modified matrix material with an organic amine having at least two amine groups per molecule to form an amine-modified matrix material.

7. The method of claim 6 further including a step of capping any unreacted amine groups on the matrix material having the sensing component, or precursor thereof, covalently attached thereto, by contacting the unreacted amine groups with a solution comprising an acetylating agent, an organic amine, and an ethereal solvent.

8. The method of claim 7 wherein the organic amine is a tertiary amine and the solution further includes a catalyst.

9. The method of claim 8 wherein the catalyst is a substituted pyridine.

10. A method of making an ionic sensor comprising:
    (a) reacting acetoxypyrenetris(sulfonyl)chloride with an amine-modified polymeric ion-permeable matrix material to form bound acetoxypyrenesulfonamide; wherein the acetoxypyrenetris(sulfonyl)chloride is made by a method comprising:
        (i) converting hydroxypyrenetrisulfonate to acetoxypyrenetrisulfonate; and
        (ii) reacting acetoxypyrenetrisulfonate with thionyl chloride and a catalytic amount of disubstituted formamide to form acetoxypyrenetris(sulfonyl)chloride;
    (b) converting the bound acetoxypyrenesulfonamide to the hydroxy form to form a sensing element; and
    (c) covering the sensing element with an opaque overcoat material.

11. The method of claim 10 wherein the polymeric ion-permeable matrix material is cellulose.

12. The method of claim 10 wherein the step of reacting acetoxypyrenetris(sulfonyl)chloride with the amine-modified polymeric ion-permeable matrix material comprises reacting them in an aqueous-based bath comprising water, an organic solvent in an amount effective to solubilize the acetoxypyrenetris(sulfonyl)chloride, and buffer salts.

13. The method of claim 10 further including a step of capping any unreacted amine groups on the matrix material having the sensing component, or precursor thereof, covalently attached thereto, by contacting the unreacted amine groups with a solution comprising an acetylating agent, an organic amine, and an ethereal solvent.

14. The method of claim 10 wherein the step of converting the bound acetoxypyrenesulfonamide to the bound hydroxy form comprises combining the bound acetoxypyrenesulfonamide with an aqueous solution having a pH of at least about 10 and an ionic strength of at least about that of a 5% aqueous sodium chloride solution.

15. The method of claim 14 wherein the aqueous solution comprises:
    (a) a base selected from the group consisting of sodium carbonate, sodium hydroxide, and mixtures thereof; and
    (b) a salt selected from the group consisting of sodium chloride, sodium acetate, sodium sulfate, and mixtures thereof.

16. A method of making an ionic sensor comprising:
    (a) applying to a surface of a first polymeric ion-permeable matrix material, a second polymeric ion-permeable matrix material having mixed therein an opaque agent;
    (b) reacting both matrix materials with an epoxide having at least two epoxy groups per molecule to covalently bond the two matrix materials together and form pendant epoxy groups;

(c) reacting the epoxy groups with an organic amine having at least two amine groups per molecule to form pendant amine groups;

(d) reacting acetoxypyrenetris(sulfonyl)chloride with the pendant amine groups in an aqueous-based bath comprising water, an organic solvent in an amount effective to solubilize the acetoxypyrenetris(sulfonyl)chloride, and buffer salts, to form bound acetoxypyrenesulfonamide; wherein the acetoxypyrenetris(sulfonyl)chloride is made by a method comprising:

(i) converting hydroxypyrenetrisulfonate to acetoxypyrenetrisulfonate; and (ii) reacting acetoxypyrenetrisulfonate with thionyl chloride and a catalytic amount of a disubstituted formamide to form acetoxypyrenetris(sulfonyl) chloride;

(e) converting the bound acetoxypyrenesulfonamide to the bound hydroxy form; and (f) capping any unreacted amine groups on the matrix material by contacting them with a solution comprising an acetylating agent, an organic amine, and an ethereal solvent.

17. The method of claim 16 wherein the first polymeric ion-permeable matrix material is cellulose, the second polymeric ion-permeable matrix material is dextran, and the opaque agent is carbon black.

* * * * *